United States Patent
Mucci et al.

(10) Patent No.: US 6,312,382 B1
(45) Date of Patent: Nov. 6, 2001

(54) METHOD AND APPARATUS FOR EXTRACTING CARDIAC INFORMATION FROM ACOUSTIC INFORMATION ACQUIRED WITH AN ULTRASOUND DEVICE

(76) Inventors: Ronald Mucci, 106 Mill St., Westwood, MA (US) 02090; Ban Dinh, 3 Chelsea St., Wilmington, MA (US) 01887; Frank R Miele, 1 Riverview Blvd. #1-006, Methuen, MA (US) 01844

( * ) Notice: Subject to any disclaimer, the term of this patent is extended or adjusted under 35 U.S.C. 154(b) by 0 days.

(21) Appl. No.: 09/440,392

(22) Filed: Nov. 15, 1999

(51) Int. Cl.$^7$ .................................................... A61B 8/00
(52) U.S. Cl. .............................................. 600/437; 600/450
(58) Field of Search ................................... 600/437, 443, 600/449, 450, 453, 441, 454, 485, 587, 490, 506; 607/45; 367/7, 135; 73/625, 626, 627

(56) References Cited

U.S. PATENT DOCUMENTS 5,156,154 * 10/1992 Valenta, Jr. et al. ................. 600/455
5,415,171 * 5/1995 Goh et al. ............................. 600/443

* cited by examiner

*Primary Examiner*—Marvin M. Lateef
*Assistant Examiner*—Ali M. Imam

(57) ABSTRACT

The present invention provides a method and apparatus for processing acoustic information obtained with an ultrasound device to generate cardiac information, such as, for example, a patient's heart rate. In accordance with the present invention, an ultrasound system is utilized to image a patient's heart to obtain acoustic information relating to the patient's heart. The acoustic information is converted into electrical information, which is then processed to extract a particular feature of interest therefrom, such as, for example, the patient's heart rate. In accordance with the preferred embodiment of the present invention, processing of the electrical signals comprises the steps of generating a time-series from a series of image frames and then performing a spectral analysis on the time-series. The features of interest are then easily extracted from the results of the spectral analysis. In generating the time-series, the same line and depth in the ultrasound envelope is used from each image frame to obtain the sample from the image frame to be used in the time-series. The samples derived from the series of image frames are concatenated together to produce the time-series. The spectral analysis, which preferably is Fourier analysis, is then performed on the time-series. Amplitude peaks resulting from the Fourier analysis are analyzed to determine the fundamental frequency, which corresponds to the patient's heart rate.

20 Claims, 5 Drawing Sheets

METHOD AND APPARATUS FOR EXTRACTING CARDIAC INFORMATION FROM ACOUSTIC INFORMATION ACQUIRED WITH AN ULTRASOUND DEVICE

TECHNICAL FIELD OF THE INVENTION

The present invention relates to ultrasound imaging and, more particularly, to a method and apparatus for processing acoustic information obtained with an ultrasound device to generate cardiac information, such as, for example, a patient's heart rate.

BACKGROUND OF THE INVENTION

Cardiac information is normally obtained using conventional devices and techniques, such as manually operating a stethoscope and listening to the patient's heart, or attaching electrodes to the patient and obtaining an electrocardiogram (ECG) which provides information about the patient's heart.

Ultrasound systems currently are utilized to obtain information about a patient's heart. However, ultrasound systems currently do not extract the patient's heart rate from the acoustic ultrasound information because it is believed that other techniques, such as ECG techniques, are better suited for this purpose. Therefore, although ultrasound systems exist that display the patient's heart rate, the heart rate is obtained using ECG techniques, which require the attachment of leads to the patient's body. Ultrasound systems comprise a probe that transmits high frequency acoustic waves into a patient's body and receives acoustic waves back scattered by objects within the patient's body. The back scattered acoustic waves, or echoes, are converted into electrical signals and the electrical signals are converted into pixels, which are displayed on a display monitor of the ultrasound system. The image displayed on the display monitor represents an anatomical image of the scanned area in the patient's body.

In many cases, it is useful to provide the technician or physician operating an ultrasound system with the patient's heart rate. This information may be useful in analyzing the image being displayed for diagnostic purposes. It would also be desirable to be able to extract cardiac rate information from the back scattered acoustic waves. This would eliminate the need to use ECG techniques or a stethoscope to obtain the cardiac information.

Accordingly, a need exists for a method and apparatus for extracting cardiac information from acoustic information acquired using an ultrasound system.

SUMMARY OF THE INVENTION

The present invention provides a method and apparatus for processing acoustic information obtained with an ultrasound device to generate cardiac information, such as, for example, a patient's heart rate. In accordance with the present invention, an ultrasound system is utilized to image a patient's heart to obtain acoustic information relating to the patient's heart. The acoustic information is converted into electrical information, which is then processed to extract a particular feature of interest therefrom, such as, for example, the patient's heart rate.

In accordance with the preferred embodiment of the present invention, processing of the electrical signals comprises the steps of generating a time-series from a series of image frames and then performing a spectral analysis on the time-series. The features of interest are then easily extracted from the results of the spectral analysis. In generating the time-series, the same line and depth in the ultrasound envelope is used from each image frame to obtain the sample from the image frame to be used in the time-series. The samples derived from the series of image frames are concatenated together to produce the time-series. The spectral analysis, which preferably is Fourier analysis, is then performed on the time-series. Amplitude peaks resulting from the Fourier analysis are analyzed to determine the fundamental frequency, which corresponds to the patient's heart rate.

These and other features and advantages of the present invention will become apparent from the following description, drawings and claims.

DETAILED DESCRIPTION OF THE PREFERRED EMBODIMENT

Figure 1:
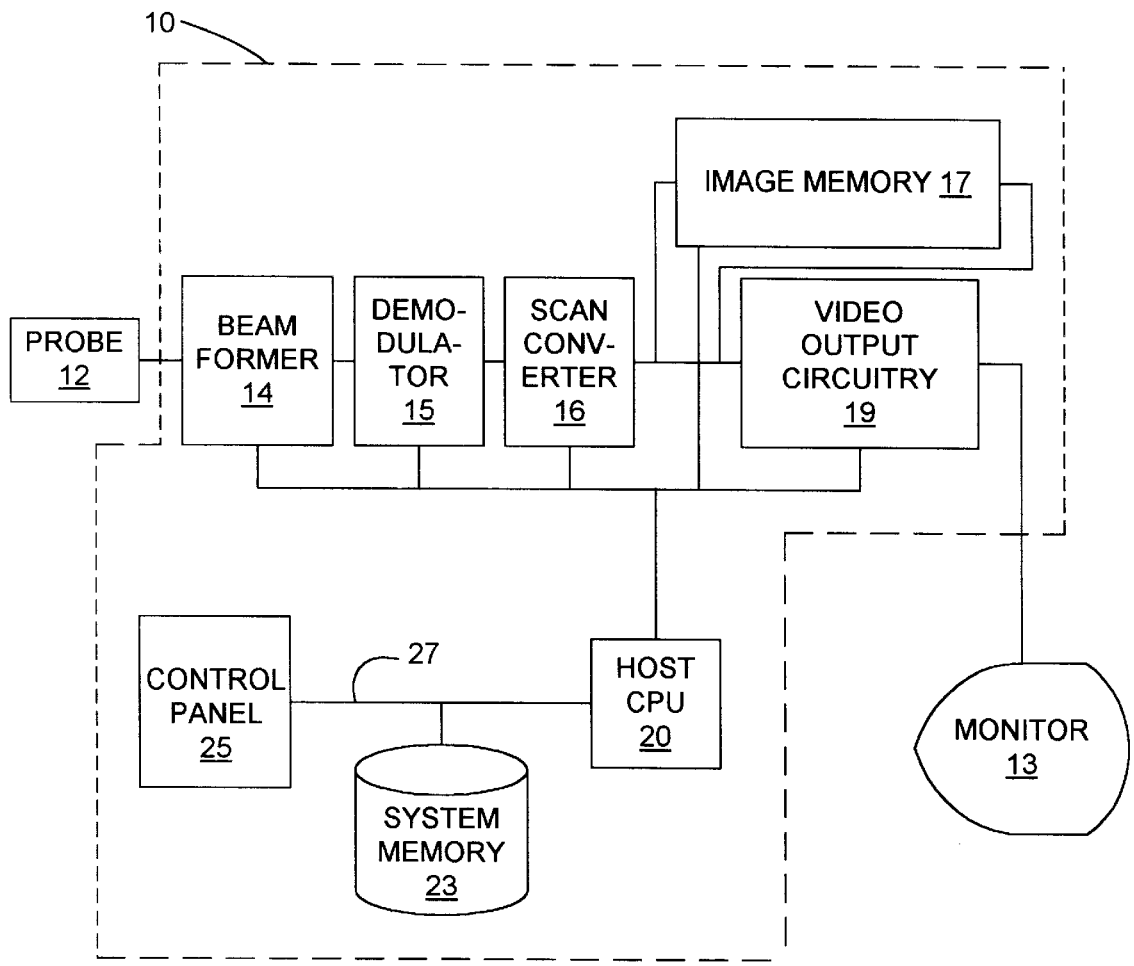
FIG. 1 is a block diagram of the electrical control circuitry of an ultrasound diagnostic device that can be utilized to acquire acoustic ultrasound image data and to process the data to extract cardiac information therefrom.

FIG. 1 is a block diagram of electrical control circuitry 10 of an ultrasound diagnostic device (not shown) which may used to acquire acoustic ultrasound image data from a patient. The electrical control circuitry 10 is electrically coupled to a probe, or transducer, 12 and to a display monitor 13. The electrical control circuitry 10 comprises a beam former component 14 that generates electrical signals that cause the probe 12 to form a shaped acoustic beam. The probe 12 projects the acoustic beam into the patient. Reshaped acoustic waves that are back scattered (i.e., echoes) by discontinuities in the patient's body are returned to the probe 12, which reconverts them into electrical signals.

These signals are beam formed by the beam former component 14 and demodulated by a demodulator component 15. The beam former component 14 and the demodulator component 15 comprise the data acquisition components of the electrical control circuitry 10. The ultrasound waves that are generated by the probe 12 normally are high frequency waves. Therefore, the acoustic waves back scattered by discontinuities in the patient's body are also high frequency waves. However, the information that is of interest in the back scattered acoustic waves corresponds to relatively low frequency variations in the amplitude of the back scattered acoustic waves over time. The demodulator component 15 separates these amplitude variations from the high frequency ultrasound signal and generates an envelope signal, which corresponds to these amplitude variations over time. The scan converter component 16 receives the envelope signal from the demodulator component 15 and allocates intensity values to the appropriate pixels in the appropriate image frame of image memory 17.

As the acoustic beam is steered in different directions by the beam former component 14, i.e., as the angle of projection of the beam is incrementally shifted, different pixels in the frames of image memory 17 are filled in with image data. The video output circuitry 19 reads the image frames out of the image memory 17 and causes them to be displayed on the monitor 13. The displayed image typically is an inverted fan-shaped slice, which corresponds to the series of beams, or lines, projected from the center of the probe 12 into the patient. Each line is comprised of a series of pixels and each point along a line corresponds to a particular depth into the patient as measured from the center of the probe surface.

The functions normally performed by the probe 12, the beam former component 14, the demodulator component 15, the scan converter component 16, the image memory 17, the video output circuitry 19 and the monitor 13 are well known to those skilled in the art of ultrasound imaging. Therefore, a detailed discussion of these functions will not be provided herein in the interest of brevity.

Each page of image memory 17 contains the data for one image frame that is to be displayed on the display monitor 13. The image memory 17 typically contains many image frames of the beating heart. The video output circuitry 19 formats the image data in accordance with a predetermined horizontal and vertical synchronization process. The synchronization process utilized by the video output circuitry 19 is dictated by the type of display monitor 13 utilized. The video output circuitry 19 also translates the data into either color data or black-and-white data, depending upon the type of data stored in image memory 17 and the requirements of the display monitor 13.

The host CPU 20 executes programs stored in system memory 23. The host CPU 20 also receives commands from the control panel 25, which correspond to entries made on the control panel 25 by a user (not shown). The CPU 20 processes these commands in a manner dictated by one or more programs being executed by the CPU 20. The host CPU 20 communicates with the control panel 25 and with the system memory 23 via a system bus 27. The commands entered by the user may correspond to, for example, operations to be performed on the ultrasound image. The host CPU 101 translates these commands into control data, which may be output to the other components of the electrical control circuitry 10 for controlling the operations thereof.

The control data sent to the beam former component 14 controls the data acquisition process performed by the beam former component 14 in conjunction with the probe 12. In accordance with the present invention, acquired image frames of the beating heart that have been stored by the scan converter component 16 in the image memory 17 are processed by the host CPU 20 in accordance with one or more algorithms to extract cardiac information from the acoustic ultrasound image information. However, it should be noted that it is not necessary that a CPU be used to perform these algorithms. Other types of hardware, such as, for example, a digital signal processor can also be used for this purpose. Also, it should be noted that the algorithms performed in accordance with the present invention can be performed solely in hardware or in a combination of hardware and software. Those skilled in the art will understand that virtually an infinite number of hardware and/or software configurations are suitable for this purpose.

In accordance with the preferred embodiment of the present invention, an estimate of a patient's cardiac rate is obtained by performing a spectral analysis (e.g., a Fourier spectral analysis) on a time-series constructed from the envelope signals associated with a series of image frames of the acquired acoustic ultrasound signal. The time-series is constructed by concatenating a single sample from the envelope signal of each image frame of a series of image frames of the beating heart. For each image frame in the series, the extracted samples correspond to the same image pixel, the same line and the same depth along the line. Once the time-series has been constructed, a spectral analysis of the time-series is performed. The cardiac information is then extracted from the results of the spectral analysis.

Figure 2:
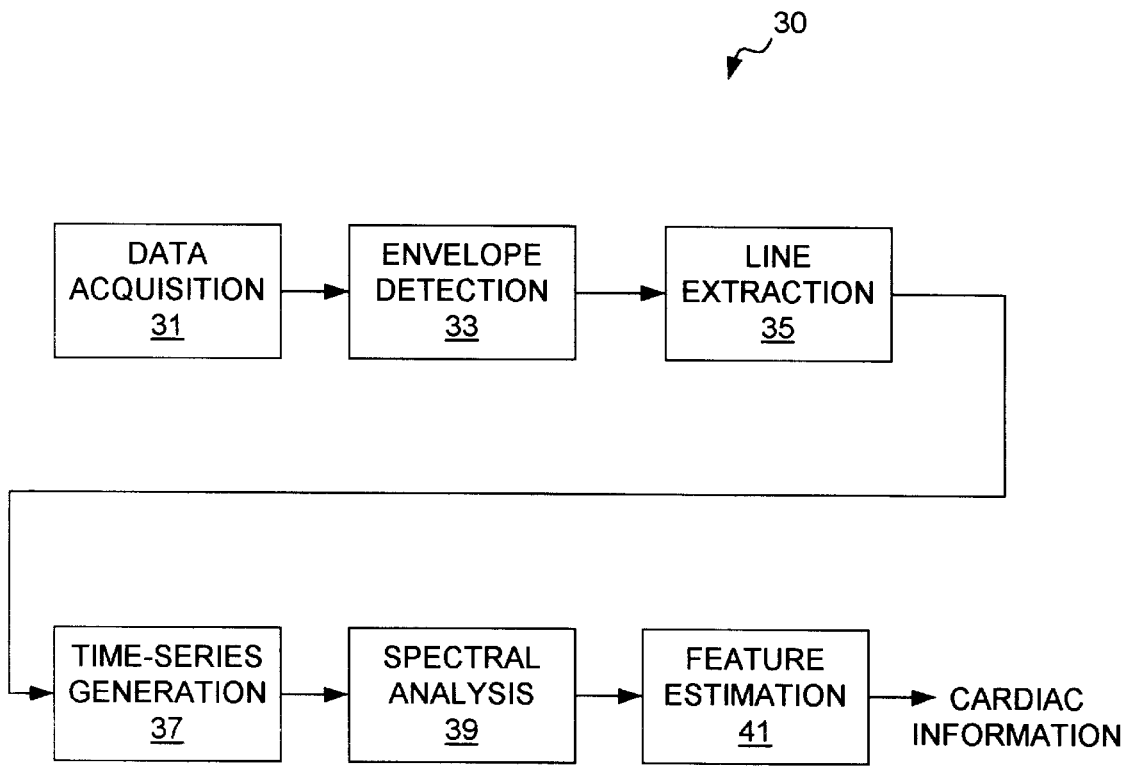
FIG. 2 is a block diagram illustrating the method of the present invention implemented by the electrical control circuitry shown in FIG. 1.

The processing steps performed by the method of the present invention are illustrated in FIG. 2, and are collectively represented by numeral 30. The acoustic ultrasound information is acquired by the beam former component 14 in conjunction with the probe 12 during the data acquisition process 31, as discussed above with reference to FIG. 1. The demodulator component 15 detects the envelope signal, which corresponds to the amplitude variations of the back scattered acoustic wave over time, as represented by block 33. The host CPU 20 then extracts a particular line of the acoustic image data contained in the envelope signal for analysis, as represented by block 35. The host CPU 20 utilizes the intensity value of a particular pixel corresponding to a particular depth along the selected line to generate a time-series over all of the image frames in the series, as represented by block 37.

Once the time-series has been generated, a spectral analysis is then performed by the host CPU 20 on the time-series, as represented by block 39. The features of interest (e.g., heart rate) are then easily estimated from the results of the spectral analysis, as represented by block 41. The host CPU 20 can be used to estimate the features of interest or the features may be estimated by a user viewing the results of the spectral analysis on the display monitor 13, as discussed below in more detail. The manner in which the features of interest can be automatically or manually estimated from the results of the spectral analysis will now be described with reference to FIGS. 3, 4A and 4B.

Figure 3:
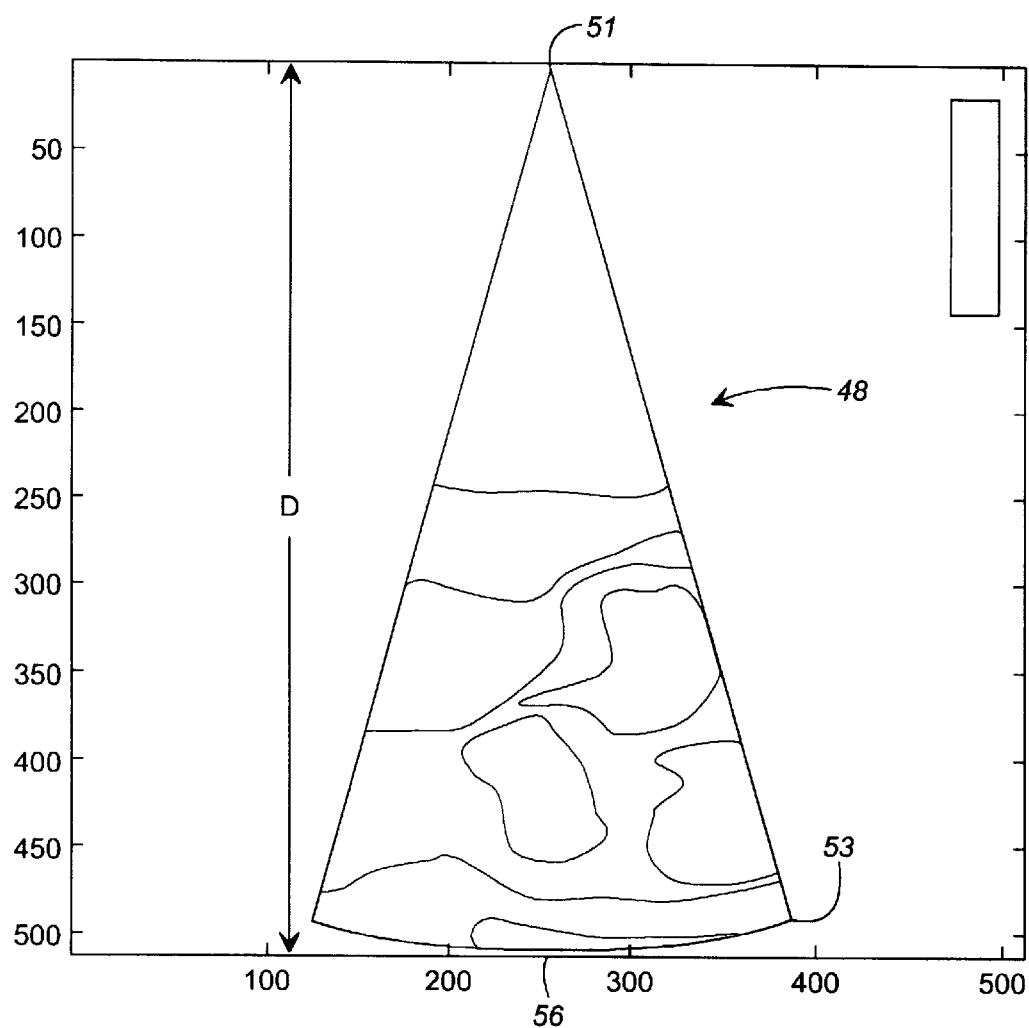
FIG. 3 is an illustration of a frame acquired by an ultrasound system and displayed on a display monitor.

FIG. 3 illustrates one image frame 48 displayed on a display device of a typical ultrasound device. The image frame 48 corresponds to one of a series of image frames of the beating heart over which the aforementioned time-series is calculated. The apex 51 of the image frame 48 corresponds to the center of the probe 12 and the depth, D, from the center of the probe 12 into the patient increases in a direction away from the apex toward the bottom arc 53 of the image frame 48. The numbers on the vertical axis of the plot correspond to pixel location at a particular depth. The horizontal axis of the plot shown in FIG. 3 corresponds to width.

In each frame, the image displayed is a 2-D slice comprised of a large number of lines, which extend from the apex 51 to the arc 53. Each line in the image corresponds to a line that was shot by the probe 12 into the patient. In performing the method of the present invention, the same line in each of the image frames is used to generate the time series. For purposes of demonstrating an exemplary application of the method of the present invention, line 21 in each of the image frames will be utilized to calculate a time-series and a spectral analysis will then be performed on the time-series. Line 21 corresponds to the center line in the frames, which is a line extending from the apex 51 to the point on the arc designated by numeral 56. The depth, D, of the location along the line 56 of the pixel utilized in the calculations is 6.4 centimeters.

Although the present invention is not limited with respect to the line that is used or with respect to the depth along the line that is used, for best results, a line which is located close to the center of the image should be used. This is because persons obtaining measurements using ultrasound devices normally position the probe so that the region of interest is centered with respect to the probe. Therefore, a line near the center of the image frame will typically provide the best image quality, as will be understood by those skilled in the art.

Figure 4A:
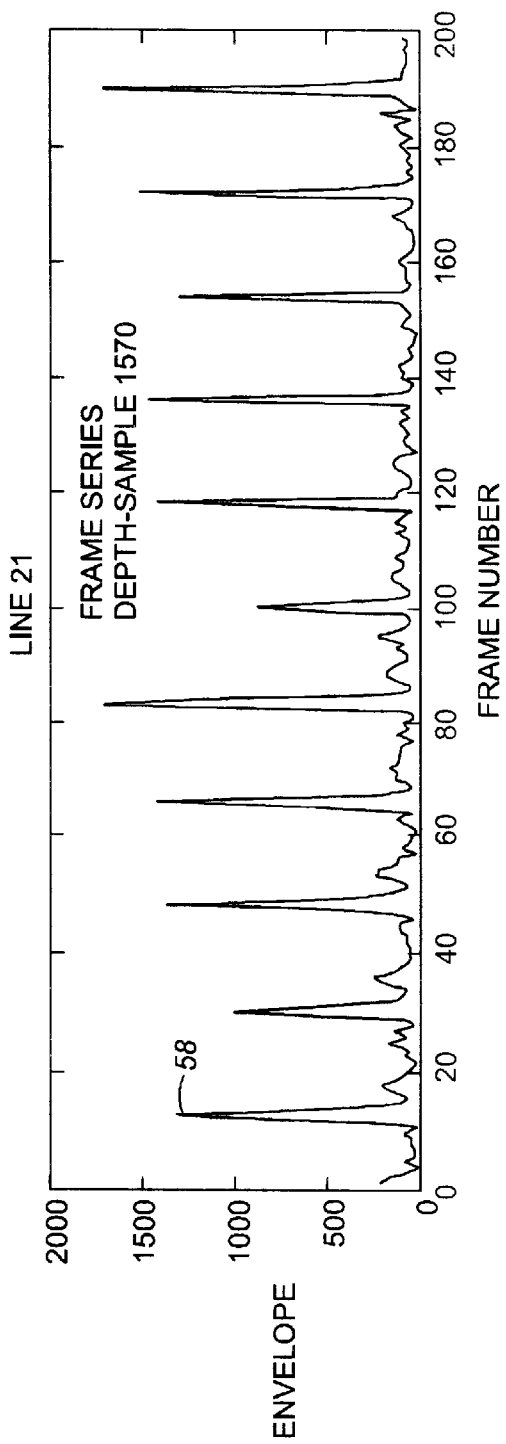
FIG. 4A is a graphical illustration of a time-series generated from the ultrasound image shown in FIG. 3.

FIG. 4A corresponds to the time-series generated for a sample pixel on line 21 at a depth of 6.4 centimeters. The periodic characteristics of the frame-to-frame derived envelope data are evident in the plot of the time-series. In this example, a cine loop was utilized, which corresponds to a series of 199 frames at a rate of 15 frames per second. However, those skilled in the art will understand that the present invention is not limited to utilizing any particular number of frames or frame rate. The cine loop is merely used for exemplary purposes.

It should also be noted that, rather than using a single sample point, i.e., a single sample pixel, a small number of pixels surrounding the analysis pixel may be averaged to obtain the sample value to be utilized in the calculations. This ensures that the sample value being utilized for any given frame is an accurate value. Since there may be some motion in the probe and/or in the patient's body, using a single sample point may sometimes result in inaccuracies. Averaging a neighborhood of pixel values can ensure the accuracy of the sample value.

However, it will be understood by those skilled in the art that performing this averaging step is not critical to the present invention. Those skilled in the art will understand that other techniques may be utilized to ensure accuracy in the sample values utilized in the calculations. For example, interpolation techniques other than averaging and estimation techniques can be utilized to obtain an accurate sample value. Such techniques are well known in the art. It should also be noted that a sample value can be obtained directly from the envelope signal of each frame, rather than first scan converting the envelope signal into pixel intensity values. Both the envelope signal and the scanconverted image contain the periodic information that can be used to generate the timeseries on which the spectral analysis will be performed.

It should also be noted that multiple sample points from multiple lines in each image frame can be processed simultaneously so that multiple heart rate estimates are obtained simultaneously. The host CPU 20 may then select the most reasonable estimate, assuming the estimates are not identical. Alternatively, the host CPU 20 may use all of the estimates to interpolate an estimate of the heart rate. For example, the host CPU 20 may average a plurality of estimates together to obtain a final estimate. Those skilled in the art will understand the manner in which the host CPU 20 may be programmed to determine a reasonable estimate from a plurality of estimates or to interpolate an estimate using a plurality of estimates. It should also be noted that the host CPU 20 may be programmed to automatically select a different sample point on a particular line, or to automatically select a different line altogether. There may be situations when the host CPU 20 is unable to obtain a good estimate of the heart rate for a variety of reasons. In this situation, the host CPU 20 may simply select a different line in the image and use a sample from that line to obtain a new estimate.

The samples utilized to calculate the time-series shown in FIG. 4A were obtained directly from the envelope signal. The vertical axis of the time-series shown in FIG. 4A corresponds to the amplitude of the envelope signals associated with each image frame of the series. The horizontal axis corresponds to the frame number. The samples for each frame have been concatenated together to produce the desired time-series. The amplitude peaks shown in FIG. 4A reflect the periodicity of the heart beat. In this example, 199 frames have been utilized to obtain the time-series. At fifteen frames per second, this corresponds to a time window of approximately 13 seconds, which is sufficiently long to capture several beats of the patient's heart. However, those skilled in the art will understand that the present invention is not limited to any particular duration of the time window utilized for generating the time-series, except that it should be of a duration sufficient to capture a few beats of the heart.

The horizontal axis has been divided into sub-series having 20 frames each for purposes of illustration. Each sub-series corresponds to a time window of approximately 1.2 seconds and contains one peak 58 that is larger than any others in that particular subseries. These peaks in amplitude correspond to an instant when the tissue of the heart moves over a location on the selected line that corresponds to the sample. In comparison to heart tissue, blood within the heart does not back scatter very much of the acoustic energy projected by the probe 12. Therefore, when the heart tissue moves away from the sample point on the line during the cycle of the heart, the amplitude of the sample will be less than when the heart tissue is over the sample point. Therefore, the rhythmic motion of the heart correlates to the periodic nature of the time-series.

Once the time-series has been generated, it may be analyzed using conventional transform techniques, such as the well known Fourier transform algorithm. As stated above, other spectral analysis techniques that are well known in the art are also suitable for this purpose, although Fourier analysis is the preferred technique. For example, another well known type of spectral analysis that is suitable for analyzing the time-series is wavelet analysis. It should also be noted that spectral analysis techniques that are developed in the future may also be suitable for this purpose. Therefore, the present invention is not limited to the particular spectral analysis technique used to analyze the time-series.

Figure 4B:
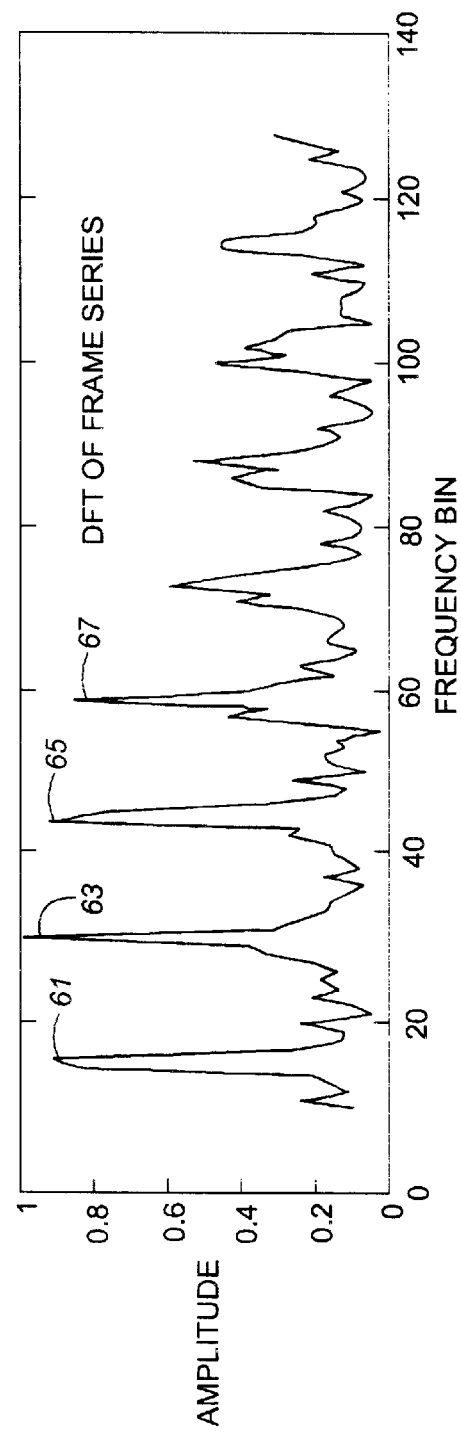
FIG. 4B is a graphical illustration of the results of a spectral analysis performed on the time-series shown in FIG. 2.

FIG. 4B is a plot of the discrete Fourier transform of the time-series shown in FIG. 4A. The horizontal axis of the plot of FIG. 4B is labeled with frequency bins, which correspond to the frequencies associated with the amplitude time-series constructed from samples of the envelope signals. Since a discrete Fourier transform is used, each of the frequency bins corresponds to an integer value, but also contain a range of non-integer values. For example, the frequency bin corresponding to integer 20 will map to a particular frequency. A range of non-integers contained in that frequency bin which range from, for example, 19.5 to 20.4 will also map to that frequency. Similarly, the frequency bin corresponding to integer 21 will map to a particular frequency and a range of non-integers contained in that frequency bin which range from, for example, 20.5 to 21.4 will also map to that frequency.

The bin numbers are mapped into frequencies by applying Equation 1:

$$F_{rt}=N_{pk}(F_s/FT_{size}),\qquad\qquad\text{(Equation 1)}$$

where $F_{rt}$ is the estimated frequency of the heart in terms of beats per second, $N_{pk}$, is the bin number, $F_s$, denotes the frame rate in frames per second, and $FT_{size}$ denotes the duration of time window over which the Fourier analysis is performed. The manner in which the spectral peaks are utilized to calculate the cardiac rate will be described below in detail. The bin number associated with that spectral peak is converted to cardiac rate, denoted $C_{rt}$ Equation 2:

$$C_{rt} = 60 N_{pk}(F_s/FT_{side}), \qquad \text{(Equation 2)}$$

where the value 60 is used to convert the rate obtained by Equation 1 into beats per minute.

In this example, the discrete Fourier transform (DFT) has been computed by padding the 199-sample envelope time-series with zeros to produce a time-series of 256 samples, which corresponds to the size of the DFT. For a frame rate of 15 frames per second, the resulting DFT has a spectral bin resolution of 15/256 Hz. The DFT has a symmetry about it and the results of the analysis can be obtained by looking at the first 128 samples, which correspond to the frequency bins labeled on the horizontal axis of the plot of FIG. 4B.

In FIG. 4B, the peak 61 corresponds to the peak associated with the most acoustic energy for frequency bins ranging from 0 to 20. This peak corresponds to the fundamental frequency, i.e., to the patient's heart rate. The manner in which the peaks in FIG. 4B are utilized to obtain a patient's cardiac rate will now be discussed. The spectral analysis will typically result in a harmonically-related series of peaks. These peaks are analyzed to determine the fundamental frequency associated with the peaks, which will correspond to the patient's heart rate. If only a single peak results from the spectral analysis, the frequency bin associated with this peak can be utilized to calculate the fundamental frequency. If the estimate of the heart rate associated with the peak is unreasonable, a different line may be automatically selected by the host CPU 20 and utilized to generate an estimate of the fundamental frequency.

The amplitude peaks can be easily detected by using straight-forward amplitude threshold comparison techniques, which are well known to those skilled in the art. Therefore, a detailed discussion of the manner in which the peaks are detected and the frequency bins with which they are associated are determined will not be provided herein in the interest of brevity.

The peak 61 corresponds to a frequency bin of 15. By applying Equation 1, a frequency, $F_{rt}$, of 0.87 Hz, or 0.87 beats per second, is obtained. By applying Equation 2, a cardiac rate, $C_{rt}$, of 52 beats per minute is obtained, which is a typical cardiac rate. These rates correspond to a Fourier transform size, $FT_{size}$, of 256, i.e., 8 bits. The peak 63 corresponds to a frequency bin of 30. By applying Equation 1, a frequency, $F_{rt}$ of 1.75 Hz, or 1.75 beats per second, is obtained. By applying Equation 2, a cardiac rate, $C_{rt}$, of 105 beats per minute.

As stated above, the host CPU 20 may be programmed to determine whether or not the calculated estimate corresponds to a reasonable heart rate. Those skilled in the art will understand that programming the host CPU 20 to distinguish between reasonable and unreasonable heart rates under a giver set of circumstances is a relatively simple task. For example, the host CPU 20 could use heart rate thresholds wherein any estimate over the threshold is determined to be unreasonable. Peaks corresponding to frequency bins beyond a particular number do not even need to be considered.

Harmonically-related spectral components contained in the DFT results may be used to discern the correct cardiac rate. Generally, this is accomplished in accordance with the present invention be detecting a series of harmonically-related peaks, by determining which peak is associated with the fundamental frequency of the harmonically-related series of peaks, and by utilizing the corresponding frequency bin to calculate the fundamental frequency. The harmonically-related peaks correspond to frequencies that are separated from the fundamental frequency, i.e., $F_{rt}$, by a known amount. For example, the frequency of the first-order harmonic is equal to $2(F_{rt})$. The frequency of the second-order harmonic is equal to $3(F_{rt})$. Therefore, a determination can be made as to whether the peak being analyzed corresponds to the fundamental frequency, i.e., the heart rate, by analyzing the frequencies associated with the harmonics.

For example, if peak 63, which corresponds to the first-order harmonic, was being analyzed to determine if it corresponded to the fundamental frequency, peak 65, which corresponds to the second-order harmonic, would not correspond to a frequency that is twice that of the frequency associated with peak 63. Rather, peak 65 would correspond to a frequency that is 1.5 times the frequency associated with peak 63. Therefore, a determination could easily be made that peak 63 does not correspond to the fundamental frequency.

Also, if for some reason, peak 61 was not detected, the fundamental frequency could be calculated by using the harmonic frequencies to determine the fundamental frequency. For example, assuming peaks 63, 65 and 67 are detected, a determination would be made that the frequency associated with peak 65 was 1.5 times the frequency associated with peak 63. The host CPU 20 would then ascertain that peak 65 corresponds to the second-order harmonic and would determine that the fundamental frequency was one third of the frequency associated with the second-order harmonic.

Similarly, a determination could be made that the frequency associated with peak 67, which corresponds to the third-order harmonic, was twice the frequency associated with peak 63 and four-thirds the frequency associated with peak 65. From this, the host CPU 20 could easily ascertain that peak 67 corresponds to the third-order harmonic and would determine that the fundamental frequency was one-fourth the frequency associated with the second-order harmonic. Those skilled in the art will understand the manner in which the algorithm of the present invention could be designed to make these types of determinations.

Figure 5:
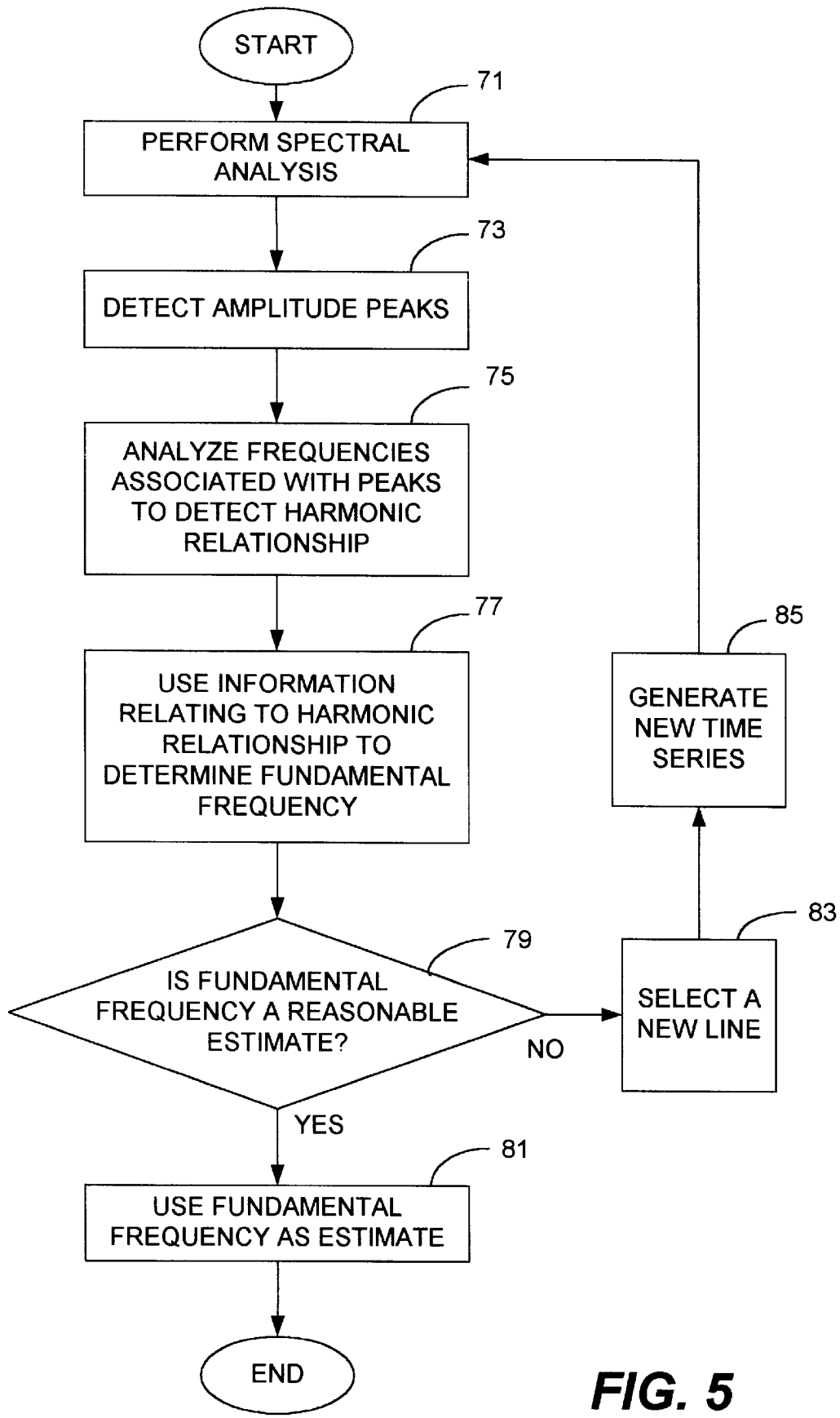
FIG. 5 is a flow chart illustrating the method of the present invention in accordance with one embodiment for extracting a patient's heart rate from results of a spectral analysis shown in FIG. 4B.

FIG. 5 is a flow chart illustrating the portion of the algorithm of the present invention that performs a spectral analysis on the generated time-series and that analyzes the results of the spectral analysis to estimate the cardiac rate of a patient. It will be understood by those skilled in the art that several variations can be made to this portion of the algorithm that are within the scope of the invention. The spectral analysis is first performed on the time-series, as represented by block 71. The host CPU 20 then detects the amplitude peaks, as represented by block 73, which can be accomplished by performing the aforementioned threshold comparison techniques. Either of Equations 1 or 2 is then utilized to determine the frequencies that are associated with the amplitude peaks and a determination is made as to whether or not a harmonic relationship between peaks can be ascertained, as represented by block 75.

If a harmonic relationship exists, the harmonic relationship is used to ascertain the fundamental frequency of the harmonic series, as represented by block 77. A determination is then made by the host CPU 20 as to whether or not the fundamental frequency corresponds to a reasonable estimate of the heart rate, as indicated by block 79. If so, the fundamental frequency is used as the estimate of the heart rate, as indicated by block 81. If not, a new line may be extracted and utilized to generate a new time-series, as indicated by blocks 83 and 85, respectively. The process then returns to block 71. As stated above, variations may be made to this process. For example, rather than performing a spectral analysis on a single time-series, multiple time-series may be generated using multiple lines and the spectral analysis may be performed on each of the time-series simultaneously. In this case, rather than determining whether the estimate is reasonable at block 79, a determination may be made as to which fundamental frequency is to be utilized as the estimate of the heart rate. Other variations will be apparent to those skilled in the art in view of the discussion provided herein.

The size of the transform and the percentage of overlap applied between successive transforms may be varied in order to achieve an appropriate mix of spectral resolution and variance of estimate, as will be understood by those skilled in the art. Also, those skilled in the art will understand that techniques other than applying Equations 1 and/or 2 may be used to extract the features of interest from the results of the spectral analysis. Equations 1 and 2 demonstrate relatively simple formulas for extracting the feature of interest, which in this example is the heart rate.

A factor that can affect the accuracy of the estimate is excess relative motion between the probe 12 and the object being imaged. Frequent changes in the imaging plane location relative to the transform size (i.e., temporal extent) can produce errors in the estimate of the cardiac rate. Therefore, it is preferable to maintain the previous estimate of the cardiac rate during intervals of excessive probe motion. The host CPU 20 will detect when excess relative motion exists between the probe 12 and the object being imaged and will use the previous estimate of the heart rate. This can be accomplished in a variety of manners.

For example, the algorithm 30 of the present invention can detect erratic changes in the estimate and cause the estimate obtained before the erratic measurements were taken to be preserved as the correct estimate. Therefore, if the heart rate is being displayed on the display monitor 13, the previous estimate preferably will continue to be displayed, even when there is excessive motion of the probe 12. However, although it is preferable to display the estimated heart rate on the display monitor 13, those skilled in the art will understand that the present invention is not limited with respect to whether or not the estimated heart rate is displayed. Also, it should be noted that, although an instantaneous estimation of the heart rate can be displayed, preferably a smoothing operation is performed on a few estimates of the heart rate so that an average heart rate is displayed. An advantage of displaying an average of the estimated heart rate is that variations in the displayed estimate caused by noise or movement of the probe 12 can be minimized or eliminated.

It is desirable to utilize a frame rate (i.e., sampling frequency) that is sufficiently large to prevent aliasing. Frequency aliasing is avoided when the time-series comprises samples that are spaced at least δ seconds apart in time, where $F_s = \delta^{-1} > 2F_{max}$ and $F_s$ denotes the maximum frequency of the spectrum of the time-series. For example, a cardiac rate of 60 beats/minute, i.e., 1 beat/second, the spectrum contains a fundamental component at 1 Hz. Therefore, a sampling rate of at least 2 samples/second, or an equivalent frame rate of 2 frames/second, should be used.

Although high frame rates are readily achievable in current ultrasound systems, high cardiac rates can be accommodated with a frame rate as low as 20 or 30 frames/second. The aliasing of the higher order harmonics, e.g., fourth or higher, can be compensated for since these components are closer in amplitude than the fundamental, as seen in FIG. 4B, and the aliasing frequency is predictable.

Those skilled in the art will understand that the present invention has been described with reference to the preferred embodiment, but that the present invention is not limited to this embodiment. Those skilled in the art will understand that variations and modifications can be made to the embodiment discussed above which are within the scope of the present invention. For example, although the method of the present invention preferably is performed by a host CPU of an ultrasound system, those skilled in the art will understand that the present invention may be external to the ultrasound system utilized to acquire the image data. Also, those skilled in the art will understand that the present invention may be performed by any suitable hardware or combination of software and hardware.

What is claimed is:

1. An apparatus for extracting a patient's cardiac rate from acoustic information acquired with an ultrasound device, the ultrasound device comprising data acquisition circuitry, the apparatus comprising:

a probe of the ultrasound device coupled to the data acquisition circuitry, the probe and data acquisition circuitry cooperating to acquire acoustic ultrasound information, the data acquisition circuitry acquiring the acquired acoustic ultrasound information at a particular frame rate, the data acquisition circuitry converting the acoustic ultrasound information into electrical envelope signals; and processing logic in communication with the data acquisition circuitry, the processing logic receiving the electrical envelope signals from the data acquisition circuitry, the processing logic being configured to generate a time-series representation from the electrical envelope signals, the processing logic being configured to perform a spectral analysis on the time-series representation, the processing logic being configured to analyze results of the spectral analysis to extract the patient's cardiac rate from the results of the spectral analysis.

2. The apparatus of claim 1, wherein the processing logic and the data acquisition circuitry are comprised by electrical control circuitry of the ultrasound device, the processing logic corresponding to the host central processing unit of the ultrasound device, the host central processing unit controlling operations of the electrical control circuitry, wherein the host central processing unit is programmed to execute an algorithm, wherein when the algorithm is being executed by the host central processing unit, the algorithm generates the time-series representation, performs the spectral analysis on the time-series representation and analyzes the results of the spectral analysis to extract the patient's cardiac rate.

3. The apparatus of claim 2, wherein the spectral analysis is a Fourier analysis.

4. The apparatus of claim 2, wherein the spectral analysis is a wavelet analysis.

5. The apparatus of claim 1, wherein the processing logic generates the time-series representation by extracting a particular line from an image frame of a series of image frames acquired by the data acquisition circuitry, the same line being extracted from each of the image frames, and wherein a particular sample corresponding to a particular depth along the extracted line is utilized as a sample when generating the time-series representation, wherein the sample extracted from the line for each image frame corresponds to the same depth in each image frame.

6. The apparatus of claim 1, wherein the processing logic generates the time-series representation by extracting a particular line from an image frame of a series of image frames acquired by the data acquisition circuitry, the same line being extracted from each of the image frames, and wherein a particular sample corresponding to a particular depth along the extracted line is utilized as a sample when generating the time-series representation, wherein the sample extracted from the line for each image frame corresponds to the same depth in each image frame, and wherein prior to extracting the lines from the envelope signals, the envelope signals are scan converted into pixels corresponding to locations on a display monitor comprised by the ultrasound device, each pixel having an image intensity value associated therewith, and wherein each sample extracted from one of the envelope signals corresponds to one or more of the pixels, and wherein the intensity values of said one or more pixels associated with each sample are utilized in generating the time-series representation.

7. The apparatus of claim 6, wherein the estimated heart rate is displayed on the display monitor.

8. The apparatus of claim 1, wherein when the spectral analysis is performed on the time-series representation, the results of the spectral analysis are expressed in terms of variations in amplitude values over time, each amplitude value contained in the results of the spectral analysis having a frequency bin associated therewith, and wherein the processing logic is configured to analyze the amplitude value variations over time and to determine which frequency bin is associated with a fundamental frequency, wherein the processing logic utilizes the frequency bin determined to be associated with the fundamental frequency to calculate the fundamental frequency, wherein the fundamental frequency corresponds to the estimated heart rate.

9. The apparatus of claim 8, wherein the processing logic analyzes the amplitude variations to detect a harmonically-related series of amplitude peaks, and wherein the processing logic analyzes information relating to the harmonically-related series to determine which frequency bin is associated with the fundamental frequency.

10. A method for extracting a patient's cardiac rate from acoustic information, acquired with an ultrasound device, the ultrasound device comprising data acquisition circuitry and a probe coupled to the data acquisition circuitry, the method comprising the steps of:

utilizing the probe and data acquisition circuitry of the ultrasound device to acquire acoustic ultrasound information, the data acquisition circuitry acquiring the acoustic ultrasound information at a particular frame rate;

utilizing the data acquisition circuitry to convert the acoustic ultrasound information into electrical envelope signals;

processing the electrical envelope signals to generate a time-series representation from the electrical envelope signals;

performing a spectral analysis on the time-series representation; and analyzing results of the spectral analysis to extract the patient's cardiac rate from the results of the spectral analysis.

11. The method of claim 10, wherein the method is performed by a host central processing unit of the ultrasound device, the host central processing unit controlling operations of the electrical control circuitry, wherein the host central processing unit is programmed to execute an algorithm, wherein when the algorithm is being executed by the host central processing unit, the algorithm performs the method.

12. The method of claim 10, wherein the spectral analysis is a Fourier analysis.

13. The method of claim 10, wherein the spectral analysis is a wavelet analysis.

14. The method of claim 10, wherein the time-series representation is generated by extracting a particular line from an image frame of a series of image frames acquired by the data acquisition circuitry, the same line being extracted from each of the image frames, and wherein a particular sample corresponding to a particular depth along the extracted line is utilized as a sample when generating the time-series representation, wherein the sample extracted from the line for each image frame corresponds to the same depth in each image frame.

15. The method of claim 10, wherein the time-series representation is generated by extracting a particular line from an image frame of a series of image frames acquired by the data acquisition circuitry, the same line being extracted from each of the image frames, and wherein a particular sample corresponding to a particular depth along the extracted line is utilized as a sample when generating the time-series representation, wherein the sample extracted from the line for each image frame corresponds to the same depth in each image frame, and wherein prior to extracting the lines from the envelope signals, the envelope signals are scan converted into pixels corresponding to locations on a display monitor comprised by the ultrasound device, each pixel having an image intensity value associated therewith, and wherein each sample extracted from one of the envelope signals corresponds to one or more of the pixels, and wherein the intensity values of said one or more pixels associated with each sample are utilized in generating the time-series representation.

16. The method of claim 10, wherein when the spectral analysis is performed on the time-series representation, the results of the spectral analysis are expressed in terms of variations in amplitude values over time, each amplitude value contained in the results of the spectral analysis having a frequency bin associated therewith, and wherein the results of the spectral analysis are analyzed by:

analyzing the amplitude value variations over time to determine which frequency bin is associated with a fundamental frequency; and utilizing the frequency bin determined to be associated with the fundamental frequency to calculate the fundamental frequency, wherein the fundamental frequency corresponds to the estimated heart rate.

17. The program of claim 16, wherein the amplitude value variations are analyzed to detect a harmonically-related series of amplitude peaks and by analyzing information relating to the harmonically-related series to determine which frequency bin is associated with the fundamental frequency.

18. A computer program for extracting a patient's cardiac rate from acoustic information acquired with an ultrasound device, the ultrasound device comprising data acquisition circuitry and a probe coupled to the data acquisition circuitry, the probe and data acquisition circuitry cooperating to acquire acoustic ultrasound information, the data acquisition circuitry acquiring the acquired acoustic ultrasound information at a particular frame rate, the data acquisition circuitry converting the acoustic ultrasound information into electrical envelope signals, the computer program being embodied on a computer-readable medium, the program comprising:

a first code segment, the first code segment processing the electrical envelope signals to generate a time-series representation from the electrical envelope signals;

a second code segment, the second code segment performing a spectral analysis on the time-series representation; and a third code segment, the third code segment analyzing results of the spectral analysis to extract the patient's cardiac rate from the results of the spectral analysis.

19. The program of claim 18, wherein the first code segment generates time-series by extracting a particular line from an image frame of a series of image frames acquired by the data acquisition circuitry, the same line being extracted from each of the image frames, and wherein a particular sample corresponding to a particular depth along the extracted line is utilized as a sample by the first code segment when generating the time-series representation, wherein the sample extracted from the line for each image frame corresponds to the same depth in each image frame.

20. The program of claim 19, wherein when the spectral analysis is performed on the time-series representation, the results of the spectral analysis are expressed in terms of variations in amplitude values over time, each amplitude value contained in the results of the spectral analysis having a frequency bin associated therewith, and wherein the third code segment analyzes the results of the spectral analysis by:

analyzing the amplitude value variations over time to determine which frequency bin is associated with a fundamental frequency, and utilizing the frequency bin determined to be associated with the fundamental frequency to calculate the fundamental frequency, wherein the fundamental frequency corresponds to the estimated heart rate.

* * * * *